(12) United States Patent
Lange et al.

(10) Patent No.: US 6,593,468 B1
(45) Date of Patent: Jul. 15, 2003

(54) ESSENTIALLY FIBER-FREE CELLULOSE ETHER WITH IMPROVED WATER RETENTION, METHOD FOR THE PRODUCTION AND USE THEREOF

(75) Inventors: Werner Lange, Visselhövede (DE); Bernd Schriewer, Walsrode (DE); Friedrich-Karl Lampert, Walsrode (DE); Wilhelm Oppermann, Bomlitz (DE); Jörn-Bernd Pannek, Fallingbostel (DE); René Kiesewetter, Fallingbostel (DE)

(73) Assignee: Wolff-Walsrode AG, Walsrode (DE)

( * ) Notice: Subject to any disclaimer, the term of this patent is extended or adjusted under 35 U.S.C. 154(b) by 0 days.

(21) Appl. No.: 09/529,705

(22) PCT Filed: Oct. 12, 1998

(86) PCT No.: PCT/EP98/06451

§ 371 (c)(1),
(2), (4) Date: Apr. 17, 2000

(87) PCT Pub. No.: WO99/20657

PCT Pub. Date: Apr. 29, 1999

(30) Foreign Application Priority Data

Oct. 20, 1997 (DE) ......................... 197 46 264

(51) Int. Cl.$^7$ ............................................. G10F 00/12
(52) U.S. Cl. .......................... 536/84; 536/90; 536/92; 536/95; 536/96; 536/97; 536/98; 536/99; 536/101; 536/124
(58) Field of Search ........................... 536/84, 90, 92, 536/95, 96, 97, 98, 99, 101

(56) References Cited

U.S. PATENT DOCUMENTS

| 2,715,124 A | 8/1955 | Miller, Jr. .................. 260/232 |
| 3,574,188 A | 4/1971 | Takehara et al. ........... 260/231 |
| 4,021,257 A | 5/1977 | Bernett ....................... 106/90 |

(List continued on next page.)

FOREIGN PATENT DOCUMENTS

| DE | 43 28 190 | 3/1995 |
| EP | 445955 | 9/1991 |
| JP | 4-161431 | 4/1992 |
| JP | 63-37143 | 2/1998 |

OTHER PUBLICATIONS

YANO "Dynamic viscoelastic Properties of Carboxymethylcellulose During Isothermal Water Sorption", Polymer, 1993, vol. 34, No. 12, pp. 2528–2532.*

(List continued on next page.)

Primary Examiner—James O. Wilson
Assistant Examiner—Everett White
(74) Attorney, Agent, or Firm—Godfried R. Akorli; Diderico van Eyl

(57) ABSTRACT

This invention relates to a process for producing a substantially fiber-free carboxymethyl cellulose which predominantly exhibits elastic properties, to the use thereof as a superabsorbent material, and to the use thereof as an adjuvant substance for achieving suitable rheological and water retention properties for the cosmetics, pharmaceutical and food sectors, and for industrial applications, e.g. as an additive for coating materials, for the sealing of cables and for use in tunnelling and in civil and underground engineering.

13 Claims, 6 Drawing Sheets

U.S. PATENT DOCUMENTS

| | | | |
|---|---|---|---|
| 4,110,226 A | 8/1978 | Swanson | 252/8.5 C |
| 4,333,968 A | 6/1982 | Nahmias | 427/173 |
| 4,404,371 A | 9/1983 | Bellmann et al. | 536/98 |
| 4,460,766 A | 7/1984 | Felcht et al. | 536/84 |
| 4,487,864 A | 12/1984 | Bermudez et al. | 524/2 |
| 4,547,570 A | 10/1985 | Garner | 536/84 |
| 4,550,161 A | 10/1985 | Felcht et al. | 536/90 |
| 4,650,716 A | 3/1987 | Gelman | 428/402 |
| 4,650,863 A | 3/1987 | Felcht et al. | 536/90 |
| 4,687,692 A | 8/1987 | Akao | 428/137 |
| 4,689,408 A | 8/1987 | Gelman et al. | 536/98 |
| 4,810,541 A | 3/1989 | Newman et al. | 428/36.7 |
| 4,952,550 A | 8/1990 | Wallach et al. | 502/404 |
| 5,087,667 A | 2/1992 | Hwo | 525/222 |
| 5,258,429 A | 11/1993 | Kniewske et al. | 524/31 |
| 5,721,295 A | 2/1998 | Bruggemann et al. | 524/44 |

OTHER PUBLICATIONS

Industrial Gums, pp. 704–729, R.L. Whistler, $2^{nd}$ Edition (month unavailable) 1972, Sodium Carboxymethylcellulose.

Chemical Abstract 87:25055 and SU 553253.

RD 349022, May 10, 1993, Scientific literature disclosure—High gel strength absorbent polymers for heat fluid absorption in packaging—including cellulose@ gum or CMC with aluminium crosslinker.

* cited by examiner

ESSENTIALLY FIBER-FREE CELLULOSE ETHER WITH IMPROVED WATER RETENTION, METHOD FOR THE PRODUCTION AND USE THEREOF

CROSS REFERENCE TO RELATED PATENT APPLICATIONS

The present patent application claims the right of priority under 35 U.S.C. §119(a)–(d) and 35 U.S.C. §365 of International Application No. PCT/EP98/06451, filed Oct. 12, 1998, which was published in German as International Patent Publication No. WO 99/20657 on Apr. 29, 1999, which is entitled to the right of priority of German Patent Application Number 197 46 264.2, filed Oct. 20, 1997.

FIELD OF THE INVENTION

This invention relates to a process for producing substantially fibre-free cellulose ethers which predominantly exhibit elastic properties, to corresponding cellulose ethers, to the use thereof as a superabsorbent material and as an adjuvant substance for achieving suitable rheological and water retention properties for the cosmetics, pharmaceutical and food sectors, and for industrial applications, e.g. as an additive for the sealing of cables (telecommunications cables, etc.).

BACKGROUND OF THE INVENTION

Superabsorbers in the sense of this invention should be understood to be products which are capable, as powders or granular materials, of absorbing liquids (water, urine, wound secretions, blood, etc.) and of retaining liquids, even under stress at a pressure of 0.1 psi–1 psi, such as that which occurs when wearing plasters, nappies, bandages and articles of hygiene of all types, as well as denture fixative cream, for example.

According to the prior art, pulverulent synthetic, polyacrylate-based superabsorbers are used for hygiene products (e.g. bandages, etc.). Their superabsorbent properties amount to about 50 g liquid per g polymer. These products are not biodegradable, however. Taking into consideration merely the proportion of what are termed disposable nappies in the entire amount of domestic waste in Germany, which is currently about 2–3% thereof, it is understandable that possible means are being sought for the replacement of synthetic products by biodegradable or compostable substances, and for furnishing the latter with technical qualities, e.g. superabsorbent properties, which are at least equivalent.

Conventional uncrosslinked carboxymethyl celluloses (hereinafter also referred to as CMCs), which are digested in the presence of a caustic solution such as caustic soda, and which are etherified with an etherification agent, such as monochloroacetic acid for example, in a mixture an organic suspension medium and water, are conventionally considered to be products which are not superabsorbent (in this respect, see R. L. Whistler in "Industrial Gums", page 704 et seq. (2nd Edition 1973)). These are usually uncrosslinked carboxymethyl celluloses which are washed with a mixture comprising suspension medium, which does not dissolve CMC, and water, and the fibrous structure of which can still clearly be identified under the microscope (see U.S. Pat. No. 2,715,124 in this respect). A carboxymethyl cellulose which is produced in this manner has different thickening properties depending on the cellulose raw material used and on the degree of polymerisation thereof (lignocellulose, cotton linters, crude linters, etc.), but generally exhibits no absorbent or superabsorbent properties. There has therefore been no lack of attempts to convert carboxymethyl cellulose, which is normally soluble in water, into an insoluble form and to improve the absorption properties by the use of crosslinking agents. Examples of crosslinking agents which have been described include 1,2-dichloroethane, epichlorohydrin, aldehydes such as formaldehyde, or metal salts which form complexes, such as chromium compounds for example (JP 04161431-A, J 63037143 A, U.S. Pat. No. 4,952,550, RD 349022 A). Moreover, there has been no lack of attempts to provide mixtures of modified carbohydrate polymers with synthetic polymers which swell in water, such as crosslinked polyacrylamides for example (EP 0131090, U.S. Pat. No. 4,021,257, U.S. Pat. No. 4,110,226, U.S. Pat. No. 3,574,188, EP 0056360, DE 3929400, DE 4328190 A1 and DE 4206857 A1). One particular disadvantage here, however, are the eco-toxicological aspects of the production, use and disposal of the crosslinked polymers. Thus special process technology measures for the protection of personnel and the environment are necessary when using polymers which are crosslinked with chloroorganic compounds or aldehydes. Moreover, the use of correspondingly crosslinked carboxymethyl celluloses in hygiene products for example (e.g. nappies, bandages) in which the CMC comes directly or indirectly into contact with the skin, can result in allergic reactions or in damage to the vegetative nervous system. Finally, the disposal of these materials can result in the contamination of groundwater due to leaching processes.

EP 0 201 895 B1 describes a process for producing a substantially non-fibrous, superabsorbent CMC, in which the superabsorbent product is obtained by dissolving the CMC in water and by the addition of a non-solvent (e.g. acetone or isopropanol).

However, the dissolution in water of a CMC or CMC cake which has already been produced, and the subsequent precipitation thereof by the addition of a non-solvent for the CMC, constitutes an additional process step which increases the cost of the process.

The object of the present invention was therefore to provide cellulose ethers, particularly a carboxymethyl cellulose, which exhibits improved absorbent properties, particularly superabsorbent properties, without the use of toxic or environmentally harmful substances. As regards the process technology employed, the object was for the product to be capable of being produced in a simple, inexpensive manner.

Surprisingly, it has been shown that simply by changing the conditions of alkalification during the production of corresponding prior art cellulose ethers, these products can be improved from a technical and eco-toxicological point of view. It has been shown that in aqueous solution, even without crosslinking reagents, the products described in the present application form high-strength gels which exhibit improved water retention. When these products are used as powders, e.g. in adhesive plasters, nappies, bandages, denture fixative creams, etc., a considerably improved water retention is observed in relation to liquids such as blood, wound secretions, urine, etc. Because toxic substances are used neither in the product itself nor in the process technology employed for the production thereof, it is possible to use these substances harmlessly for food, cosmetics and pharmaceutical applications, in addition to their industrial applications. Moreover, compared with the prior art, the water-soluble cellulose ethers which are produced according to the invention exhibit different rheological properties, particularly elastic properties, due to which it is possible to differentiate them from conventional cellulose ethers, particularly CMCs. The consequence of this is that the products which are claimed according to this invention—on their own or in combination with additional adjuvant substances—can even be used in areas in which conventional cellulose ethers exhibit deficiencies, e.g. due to shortcomings in their limits of flow (e.g. in the construction of underground curtain walls and uncased concrete piles, etc., or in coating materials (dispersion or silicate paints, etc.)).

DETAILED DESCRIPTION OF THE INVENTION

Figure 1:
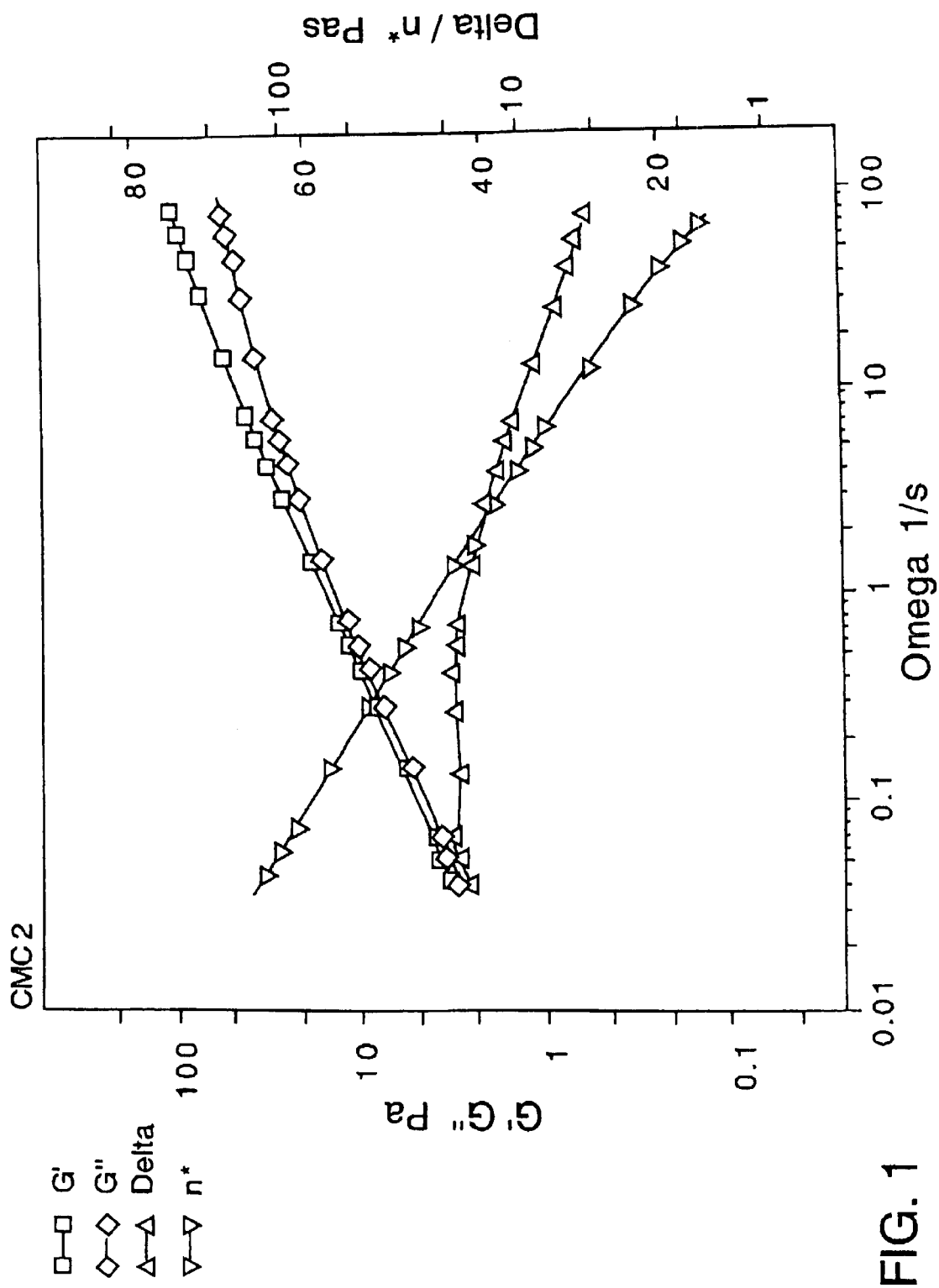
FIGS. 1–4 show the storage modulus G', the loss modulus G"", the complex viscosity η* and the phase angle as a function of angular frequency for the individual products.
Figure 2:
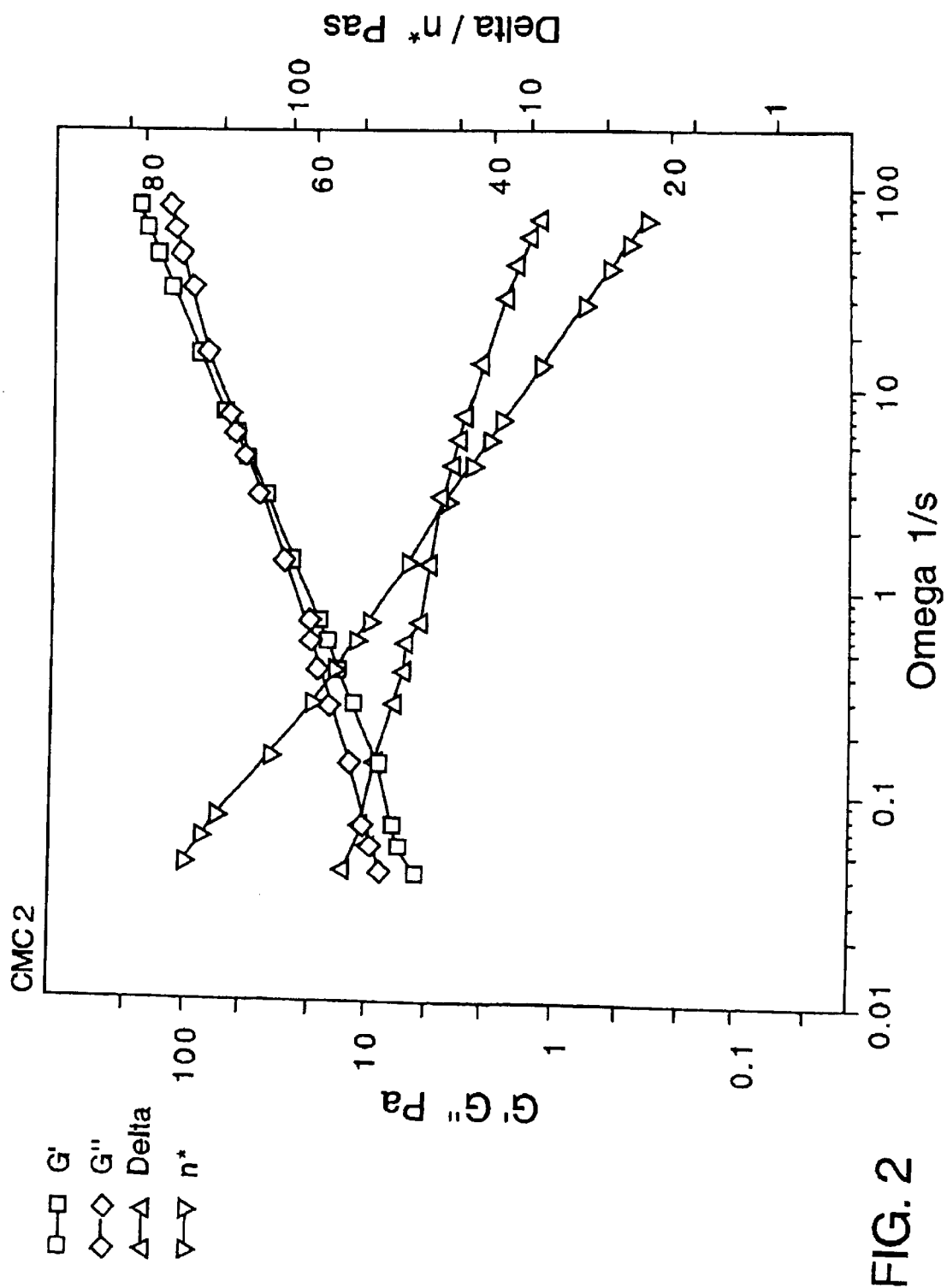
Figure 3:
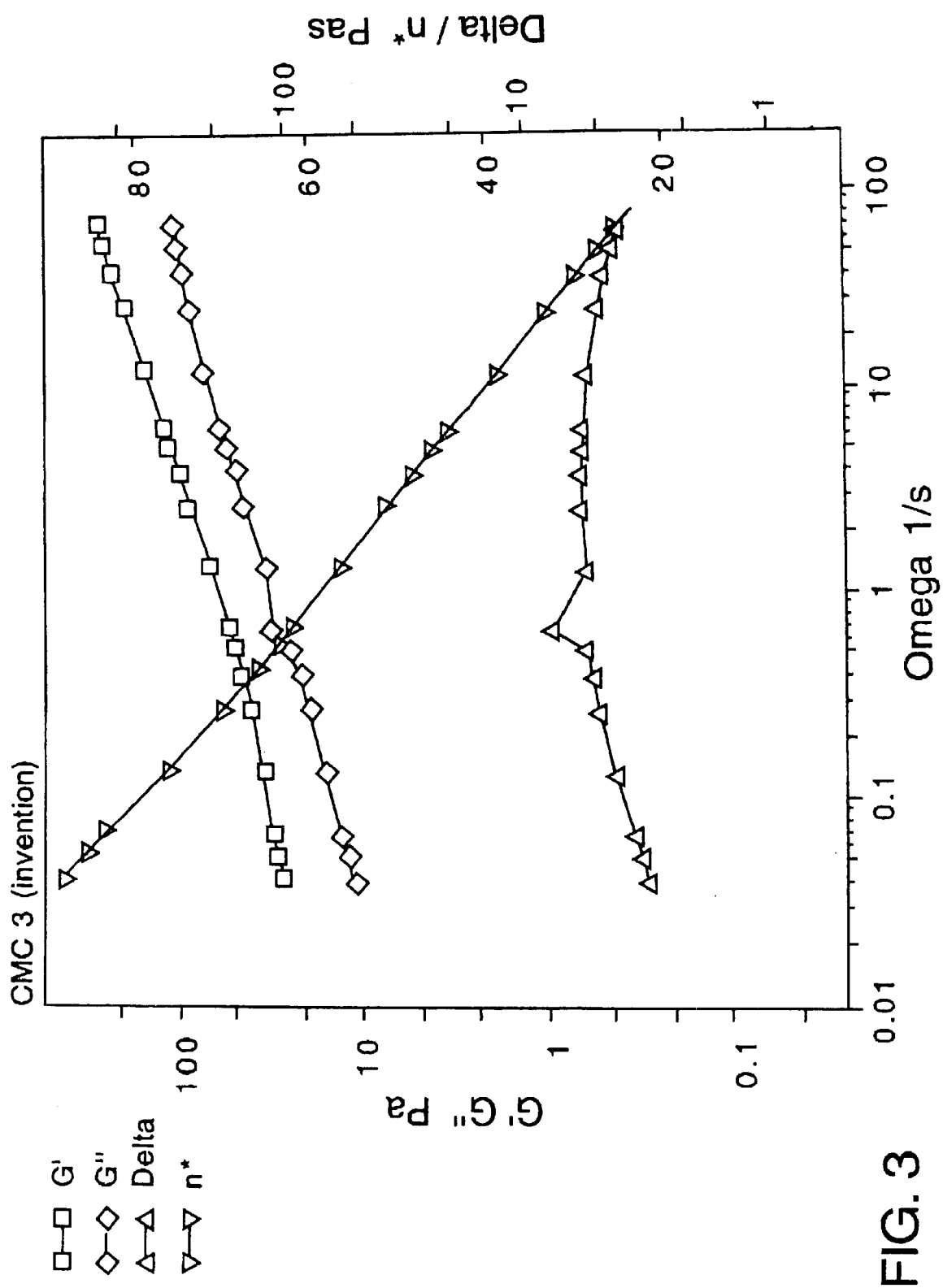
Figure 4:
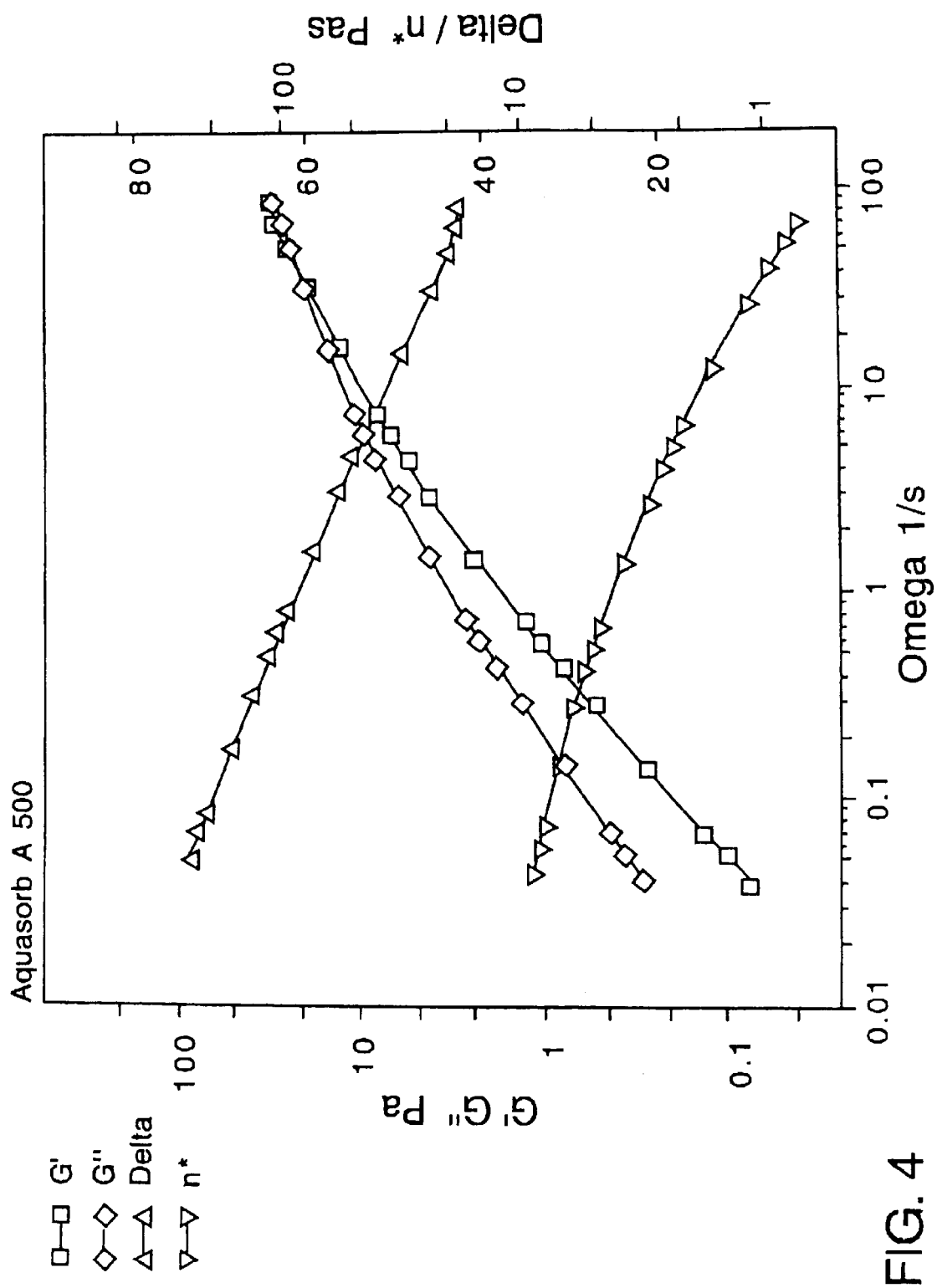

Moreover, due to the very high viscosities which they produce, it is possible to reduce the amounts of cellulose ethers which are used in existing applications without having to accept technical disadvantages by so doing. The requirement is thereby addressed of further reducing the proportion of additives in various formulations, for cosmetics for example (e.g. hair shampoos, etc.), for toxicological reasons. For engineering applications, e.g. for the construction of underground curtain walls and tunnels, the reduced use of the products claimed according to the present invention is accompanied by improved toxicological properties, e.g. reduced COD and TOC values in the soil and in the waste water, etc.

The present invention at the same time describes a process for producing a substantially fibre-free cellulose ether, particularly a carboxymethyl cellulose (CMC), which exhibits predominantly elastic properties as well as superabsorbent properties. The claimed cellulose ether (particularly CMC) has an absorbency of at least 30 g liquid per gram of cellulose ether, and is suitable for achieving appropriate rheological and water retention properties for the cosmetics, pharmaceuticals and food sectors, as well as being suitable for industrial applications e.g. for coating materials (e.g. dispersion or silicate paints, etc.) or for civil and underground engineering (tunnelling, underground curtain wall construction, etc.). The process is characterised by the following steps:

1. The use of a cellulose with an average degree of polymerisation (AP) of at least 1000, particularly >2000–3500, employing raw materials which are suitable for this purpose, such as lignocelluloses and pine celluloses, linters or crude linters, as well as mixtures thereof.
2. The use of an aqueous-organic suspension medium for producing a cellulose ether, preferably carboxymethyl cellulose, sulphoethyl cellulose, methyl or methylhydroxyalkyl cellulose ethers (MHEC, MHPC) or hydroxyalkyl cellulose ethers (HEC, HPC), which suspension medium is preferably isopropanol-water, acetone-water, methanol-water, ethanol-water or tertiary-butanol-water or mixtures thereof which have a total water content—with respect to the cellulose, suspension medium, sodium hydroxide and etherification agent (such as chloroacetic acid or vinylsulphonic acid, etc.)—of at least 11 by volume and at most 28% by volume, preferably 12.5–25% by volume, particularly 13–20% by volume, most preferably 13.5–18% by volume, and an amount of alkali, e.g. sodium hydroxide, of at least 1.8 mol–2.6 mol, preferably 2.0–2.5 mol, particularly 2.1–2.4 mol/mol glucose unit.
3. Production of a superabsorbent cellulose ether, particularly CMC, according to at least one of the aforementioned points, characterised in that an amount of etherification agent, particularly monochloroacetic acid, of 0.4–2.5 mol, particularly of 0.5–1.8 mol, preferably 0.6–1.5 mol/mol glucose is required for the production of the cellulose ether, particularly a carboxymethyl cellulose.
4. Etherification, purification, drying and manufacture in the customary, known manner, wherein the cellulose ether according to the invention, particularly CMC, which is thus obtained has a fibre content of <1%, an average degree of substitution (AS) by ether groups, particularly carboxymethyl groups, corresponding to AS=0.2–1.5, particularly from 0.3–1.2, an absorption capacity of >30 g liquid/gram cellulose ester, particularly >35 g liquid/gram cellulose ester, a total salt content (sodium chloride, sodium glycolate) of <1%, and a particle size distribution as adjusted by grinding and sieving of 100%<2 mm, 100%<0.5 mm and at least 80%<0.075 mm.

Each application makes it necessary to match the physicochemical properties (viscosity and molecularity, molecular weight distribution, particle size distribution, rheology, substitution, particle morphology, fibre content, etc.) of the respective cellulose ether to the particular requirements of the application technology concerned. In order to provide an absorbent cellulose ester, particularly CMC, or a cellulose ester such as this which exhibits the optimum superabsorbent properties such as those described here, for example for adhesive plasters, nappies, bandages, etc., the average degree of polymerisation (AP), the average degree of substitution (AS), the fibre content and the particle morphology have to be accurately matched to each other.

The use of celluloses or cellulose mixtures which have average degrees of polymerisation >1000, particularly from >2000–3500, is necessary because cellulose ethers, particularly CMC, otherwise either have absorption capacities which are too low or no longer exhibit absorbent properties at all. Products of large particle size likewise have surface areas which are too low and thus, in association therewith, exhibit insufficient absorption.

Achieving a suitable average degree of substitution (AS) by ether groups, particularly carboxymethyl groups, is just as crucial. If the AS is too low (<0.2), the product is insoluble in water and is only capable of swelling to a slight extent, or it contains fibres and only exhibits slight absorbent properties. In contrast, degrees of substitution (AS) of >1.5 result in no further improvement of the properties of the product as regards solubility and absorbency. Etherification becomes increasingly uneconomic due to the repeated use of etherification reagent or due to multiple repetition of the etherification step, and, on account of the larger amount of salt formed or due to the increased solubility of the cellulose ether, particularly CMC, can result in problems during work-up, due to prolonged wash cycles or pronounced swelling of the cellulose ether, particularly CMC, when aqueous washing media are used. Moreover, the biodegradability of the product becomes increasingly poor as the degree of substitution increases.

Achieving the low fibre content of <1% which is necessary for a high absorption is effected via the use of suitable amounts of caustic solution, such as caustic soda for example, and by converting crystalline regions of the cellulose into amorphous regions, and is also effected by the amount of etherification agent, such as monochloroacetic acid or the sodium thereof, vinylsulphonic acid, methyl chloride, hydroxyalkylating reagents such as ethylene oxide or propylene oxide or mixtures thereof for example.

Accordingly, the function of the aqueous-organic suspension medium (slurry) is to distribute the mixture of water and alkali or etherification agent in the reaction medium and to convert over-crystallized regions of the cellulose into under-crystallised regions thereof, so as thus to ensure a substantially homogeneous distribution of the caustic solution and of the subsequent etherification agent. Isopropanol-water, acetone-water, methanol-water, ethanol-water or tertiary butanol-water mixtures or binary or ternary mixtures of the aforementioned suspension media with water are preferably used as aqueous-organic suspension media. There is no restriction to defined suspension media, since other mixtures which are not explicitly cited here are also successful (see EP 0080678, EP 0161607, EP 0126959).

The amount of water which is added to the suspension medium serves to facilitate a satisfactory swelling capacity of the cellulose at the commencement of alkalification, in order thus to ensure the optimum accessibility of the alkaline cellulose to the reagents used (see U.S. Pat. No. 4,547,570, for example). It is known to one skilled in the art that too high a proportion of water in the suspension medium is uneconomic, since this results in a deterioration in the yield or etherification reagent (U.S. Pat. No. 4,547,570), so that the process is made more expensive unnecessarily. Furthermore, the proportion of gel structures increases with increasing water content in the suspension medium, and can result in problems during work-up (see SU-B 553253; CA87,1977, Ref. 25055 f and Houben-Weyl page 2054), so that the reaction is not viable for process technology and economic reasons, or is associated with corresponding disadvantages. Hitherto, improvements in process technology have therefore been concerned with keeping the water content which is necessary for the reaction low during the alkalification and etherification phase, in order thus to ensure high yields of product.

Surprisingly, it has now been ascertained that the water balance during the etherification or alkalification of the cellulose ether, particularly during the production of carboxymethyl cellulose, is of pronounced importance for controlling the water retention in the finished product and for the rheology which is necessary for the application thereof.

The cellulose ethers which are claimed according to the present invention are completely soluble in water, exhibit a decisive improvement in superabsorbent properties when used as powders, exhibit a rheology in solution which differs from that of conventional products (higher proportion of elasticity), and can be produced by the process described below, either by modifying a cellulose ether or from cellulose directly. There is no limitation to defined cellulose ethers, since the present invention does not relate to the type and amount of the etherification reagent. Ionic cellulose ethers (e.g. carboxymethyl cellulose, sulphoethyl cellulose, carboxymethylsulphoethyl cellulose, etc.) can therefore be produced by the process which is claimed according to the present invention, as can non-ionic cellulose ethers (e.g. methyl cellulose, methylhydroxyethyl cellulose, methylhydroxypropyl cellulose, hydroxyethyl cellulose, hydroxypropyl cellulose, etc.), as can mixed ethers comprising ionic and non-ionic components (e.g. carboxymethylhydroxyethyl cellulose, carboxymethylhydroxypropyl cellulose, methyl-carboxymethyl cellulose, hydroxypropyl-sulphoethycellulose, hydroxyethyl-sulphoethyl cellulose, etc.), as well as ionic or non-ionic ternary mixed ethers which contain alkyl, aryl or hydroxyalkyl groups and long chain, hydrophobic hydrocarbon radicals (e.g. hydrophobically modified HECs or hydrophobically modified HPCs). It is also possible to use physical mixtures of the aforementioned cellulose ethers, wherein the cellulose ethers which are claimed according to the present invention can be used as a mixture with conventional synthetic polymers (polyvinyl alcohols, polyvinyl acetates, polyacrylamides, etc.) or with other semi-synthetic polymers (cellulose ethers, cellulose esters, starch esters, starch ethers) or with natural polymers (alginates, starches, chitosan, chitin, lignocelluloses, pine celluloses, cotton linters, microcrystalline cellulose, lignin, etc.). It is also possible to use what are termed industrial cellulose ethers or mixtures of cellulose ethers, which are partially purified or which contain salts. Purified cellulose ethers, such as those which are required for use in foodstuffs, pharmaceuticals or cosmetics, are claimed in particular, however.

The concentration of alkali or the water content during the alkalification and etherification phase is crucial to the production of the cellulose ethers which are claimed according to the invention. Alkalification can be effected so that the total amount of alkali and the requisite amount of water are placed in the vessel at the commencement of the alkalification phase. In the course of this procedure, the etherification agent can be present, on its own or optionally with additional amounts of a second etherification agent, before or during alkalification. The etherification agent is almost always added after the addition of the total amount of alkali or of a part thereof. The alternate addition of alkali and etherification agent is usually effected in portions in a plurality of steps.

Caustic soda or caustic potash are preferably used as the alkali. The requisite amount of water can be added to the aqueous-organic suspension medium (slurry) together with or successively with the alkali, which is used in the form of prills for example. It is also possible to add part of the water or the total amount of water directly to the slurry with the alkali as a caustic solution. In this respect it is crucial that the total water content—with respect to cellulose, suspension medium, sodium hydroxide and etherification agent (such as chloroacetic acid or vinylsulphonic acid, for example)—is adjusted so that it amounts to at least 11% by volume, particularly 12.5–25% by volume, preferably 13–20% by volume, most preferably 13.5–18% by volume. If the process for the production of the cellulose ether is modified so that alkalification or etherification is carried out by a dry or semi-dry procedure practically without suspension medium, production of the product which is claimed according to the invention is conducted so that the amount of water during the alkalification and etherification step is at least 23 mol/mol glucose and is at most 45 mol/mol glucose, particularly 26–40 mol/mol glucose, most preferably at 27–35 mol/mol glucose.

The properties which are modified by comparison with those of prior art cellulose ethers can be demonstrated by the determination, in a viscometer, of the storage modulus G', the loss modulus G", the complex viscosity $\eta^*$ and the phase angle $\delta$ or the loss factor tan $\delta$ as a function of the angular frequency $\Omega$.

Thus, for aqueous solutions of these cellulose ethers which have concentrations up to a maximum of 0.5% by weight, it can be shown the value of the loss factor tan δ is less than that of prior art cellulose ethers, is substantially irrespective of the angular frequency, and at an angular frequency of 1 Hz is less than 1.0, and in particular is less than 0.8.

Rheological characterisation of the cellulose ethers which are claimed according to this invention, particularly CMC, was performed on products which had a residual salt content <3%, particularly <0.5%. The residual salt content is defined as the salt content in the final product which occurs due to secondary reactions of the etherification agent with the alkali or of the alkali with the neutralising agent which is optionally used (e.g. sodium or potassium chloride, sodium or potassium acetate, sodium or potassium glycolate, etc.). Moreover, only deionised water was used for the rheological characterisation of the products claimed according to the invention, in order to prevent any gel formation or complex formation with polyvalent cations for example.

In the cellulose ethers which are claimed according to this invention and which are further described below, the average degree of substitution (AS) denotes the number of substituted hydroxyl groups per anhydroglucose unit in the cellulose. The expression "absolutely dry substance" should be understood to mean the air-dried crude product less the moisture content thereof.

"Transmission" means the fraction of transmitted light as a percentage of the incident light during passage through an optical cell filled with an 0.5% by weight solution of aqueous cellulose (d=10 mm, wavelength λ used=550 nm (Hitachi spectrophotometer, Model 101, Hitachi Ltd., Tokyo/Japan)).

In order to determine the complete solubility in water, an amount of air-dried, purified cellulose ether was weighed in which corresponded to 500 mg of the absolutely dry substance, and was dissolved in 199.5 ml distilled water. This solution was filtered completely, under suction, through a G2 glass filter funnel which had been weighed after drying to constant weight at 120° C. The filter crucible was subsequently washed five times with 100 ml distilled water each time, in order to remove portions of dissolved cellulose ether adhering thereto. The glass filter crucible was dried to constant weight at 120° C. again and was re-weighed. The insoluble fraction was determined from the difference in weight, and the percentage content of soluble cellulose ether was calculated therefrom. Cellulose ethers which had a water-soluble fraction greater than 99.5% were deemed to be completely soluble within the range of accuracy of the measurements.

The invention is explained in more detail below with reference to various examples of embodiments.

EXAMPLES

Example CMC 1 (Comparative Example 1)

Production of a carboxymethyl cellulose corresponding to the prior art (≡Walocel VP-C-2204 PP).

137 parts of a finely ground, bleached, refined linter cellulose (moisture content 5.3%) were introduced into a cylindrical reaction vessel, the temperature of which could be controlled in a suitable manner and which was fitted with a suitable stirrer unit. The cellulose was suspended in 2805 ml isopropanol. After adding 295 ml water and 76.8 g sodium hydroxide pellets (prills), the batch was heated to 60° C. and was alkalified for 80 minutes at this temperature.

113.8 g monochloroacetic acid (79.8%) were then added. The batch was heated to 70° C. over 10 minutes and was etherified for 120 minutes at this temperature. The product was filtered off and was washed with a mixture of 70 parts methanol and 30 parts water until free from salt. The product was subsequently dried at 50° C. in a circulating air oven.

Example CMC 2 (Comparative Example 2)

In Example 2 the amount of sodium hydroxide pellets was reduced to 60.1 g, but all the other amounts remained unchanged.

In order to produce the carboxymethyl cellulose which is claimed according to the invention (sample 1), the formulation described in Example 1 (Walocel VP-C-2204 PP) was altered by increasing the proportion of water to 419 ml. The viscosities, solids contents and characteristic analytical data (degree of substitution, sodium chloride content, fibre content) which were obtained are listed in Table 1, where they are also compared with a commercially available product of the Aquasorb A 500 type.

TABLE 1

Measured physical quantities of the carboxymethyl celluloses used for comparison

| CMC No. | Viscosity [mPa.s][1] | Solids content [%] | AS[2] | NaCl [%] | Transmission [%][3] |
|---|---|---|---|---|---|
| CMC 1 | 6980 | 4.8 | 0.82 | 0.52 | 99.8 |
| CMC 2 | 7220 | 4.9 | 0.75 | 0.75 | 97.5 |
| CMC 3 (invention) | 15,940 | 5.4 | 0.73 | 0.11 | 100 |
| Aquasorb A 500[4] | 7520 | 4.2 | 0.57 | 0.25 | 99.2 |

[1] Brookfield, LVT, 30 rpm, spindle 4, T = 25° C., c = 1%
[2] Degree of substitution by carboxymethyl groups
[3] Hitachi spectrophotometer Model 101, 10 mm optical path length, λ = 550 nm
[4] sample obtained from Hercules, USA.

Comparative tests of swelling capacity were performed on the carboxymethyl cellulose samples as characterised above. The procedure was as follows: exactly 200 mg carboxymethyl cellulose were introduced into a tea bag which was subsequently closed. 150 ml of a 0.9% solution of sodium chloride were introduced into a crystallising dish (to give a height of fill of about 2 cm). The tea bag was placed horizontally on the salt solution for 10 minutes. After allowing it to drain for 1 minute, the swelling capacity was determined by a final weighing. The procedure was repeated using an empty tea bag as a zero sample. The absorption was calculated from the following expression:

Absorbed liquid in grams per gram of sample:

$$\text{Absorption} = \frac{(\text{final weight}) - (\text{zero sample} - \text{initial weight})}{CMC \text{ weighed in}}$$

High values denote very good values of water retention. Table 2 is a summary of the results. Before testing, the samples were adjusted to a particle size distribution of 100%<2 mm, 100%<0.5 mm and 80%<0.075 mm by grinding and sieving. The swelling capacity was firstly determined on the native material, i.e. on the material without temperature loading, and secondly after thermal loading (15 minutes) at 180° C.

TABLE 2

Comparative swelling tests

| Sample | Absorption[1] | Absorption after treatment at 180° C. (15 minutes) [g/g] |
|---|---|---|
| CMC 1 | 22.3 | 23.5 |
| CMC 2 | 24.9 | 20.1 |
| CMC 3 (invention) | 42.0 | 43.3 |
| Aquasorb A 500[2] | 24.1 | 26.6 |

[1]double determination in tea bag Type KC 542, width 76 mm
[2]sample obtained from Hercules (see Table 1)

It was shown that CMC sample 3, both before heat treatment and after heat treatment at 180° C., exhibited improved superabsorbent properties compared with those of the commercial products which are customarily used (e.g. CMC 1 and Aquasorb A 500).

Gel solidities were also determined using the products described above. Solutions of different concentrations were made up, and solutions of the same concentration were tested for gel solidity in a texture analyser. The results are given in Table 3.

TABLE 3

Comparative gel solidities[1]

| Product | Solidity [g] | Concentration [%] |
|---|---|---|
| CMC 1 | 25 | 1.25 |
|  | 45 | 1.50 |
|  | 89 | 2.00 |
| CMC 2 | 19 | 1.25 |
|  | 31 | 1.50 |
|  | 54 | 2.00 |
| CMC 3 (invention) | 36 | 1.25 |
|  | 56 | 1.50 |
|  | 99 | 2.00 |
| Aquasorb A 500 | 20 | 1.25 |
|  | 35 | 1.50 |
|  | 55 | 4.00 |

[1]Depth of penetration 10 mm, measuring body TA 11; velocity 1.0 mm/sec.

A comparison of the samples with each other shows that differences between the solidities of the gels became increasingly pronounced with increasing concentration. However, even at concentrations <2%, the products which are claimed according to the invention exhibited solidities which were considerably higher than those of the comparative samples.

In order to test the water retention capacity of the dissolved superabsorber under conditions relevant to application technology, a solution of the corresponding CMC sample was introduced into a crystallising dish with a diameter of 5.5 cm and a height of 1.2 cm (the dish was thus filled to the brim). Two circular pieces, which had a diameter somewhat larger than that of the crystallising dish, were previously cut from a commercially available domestic towel (Zewa brand). Both pieces were laid exactly on top of one another and were placed together on the product surface. A plate with a weight of 114 g was placed on this arrangement to stabilise it, and ensured good contact between the two pieces of domestic towel and the product. Thereafter, the arrangement was turned by 180°. 5 seconds elapsed between placing the pieces of domestic towel and turning the arrangement by 180°. The amount of water absorbed by the piece of domestic towel which had not been in direct contact with the product was determined after 1 minute by differential weighing. Table 4 gives the relative water absorption as a percentage.

TABLE 4

Comparative water retention capacity of dissolved superabsorbers under pressure

| Sample | Relative water absorption [%][1] |
|---|---|
| CMC 1 | 48 ± 3 |
| CMC 2 | 62 ± 3 |
| CMC 3 (invention) | 10 ± 3 |
| Aquasorb A 500 | 20 ± 3 |

[1]Water absorption for domestic towel (Zewa brand): wetted paper area 24 cm$^2$; mean values from 5 measurements.

As described above, polyacrylate-based superabsorbers are not biodegradable or are very difficultly biodegradable. The products which are claimed according to the invention are considerably more degradable than are conventional cellulose ethers.

The Zahn-Wellens method was used to determine the biodegradability of the aforementioned products. The product denoted above as CMC 3 (invention) was tested for degradability according to DIN EN 29888 by comparison with a conventional carboxymethyl cellulose ether of the Walocel VP-C-2204 PP type (a commercial product of Wolff Walsrode AG). The concentration of the test substances in the test was 0.5 g/l (corresponding to a DOC content of about 200 mg/l). Diethylene glycol, which exhibits the highest degree of degradability and must thus be assessed as "biodegradable", was used as the reference substance for both products. The concentration of inoculant (activated sludge from the Bomlitz sewage works) in the batches was about 0.3 g/l. The DOC contents were determined photometrically by means of an optical cell test (supplied by the Dr. Lange company). The results in Table 5 show that the CMC which is claimed according to this invention is considerably more degradable than are conventional cellulose ethers.

TABLE 5

Results of DOC determination and of biodegradability[1]

| Sample | Initial concentration DOC [mg/l] | After 7 days DOC [mg/l] | After 7 days Degradation [%] | After 28 days DOC [mg/l] | After 28 days Degradation [%] |
|---|---|---|---|---|---|
| Blank value | 1.8 | 1.7 | — | 2.6 | — |
| Reference[2] | 218 | 184 | 16 | 49.9 | 78 |
| CMC 3 (invention) | 192 | 148 | 23 | 129 | 34 |
| Walocel VP-C-2204 PP | 154 | 154 | 0 | 153 | 1 |

[1]DOC = dissolved, organically bound carbon
[2]diethylene glycol

Figure 5:
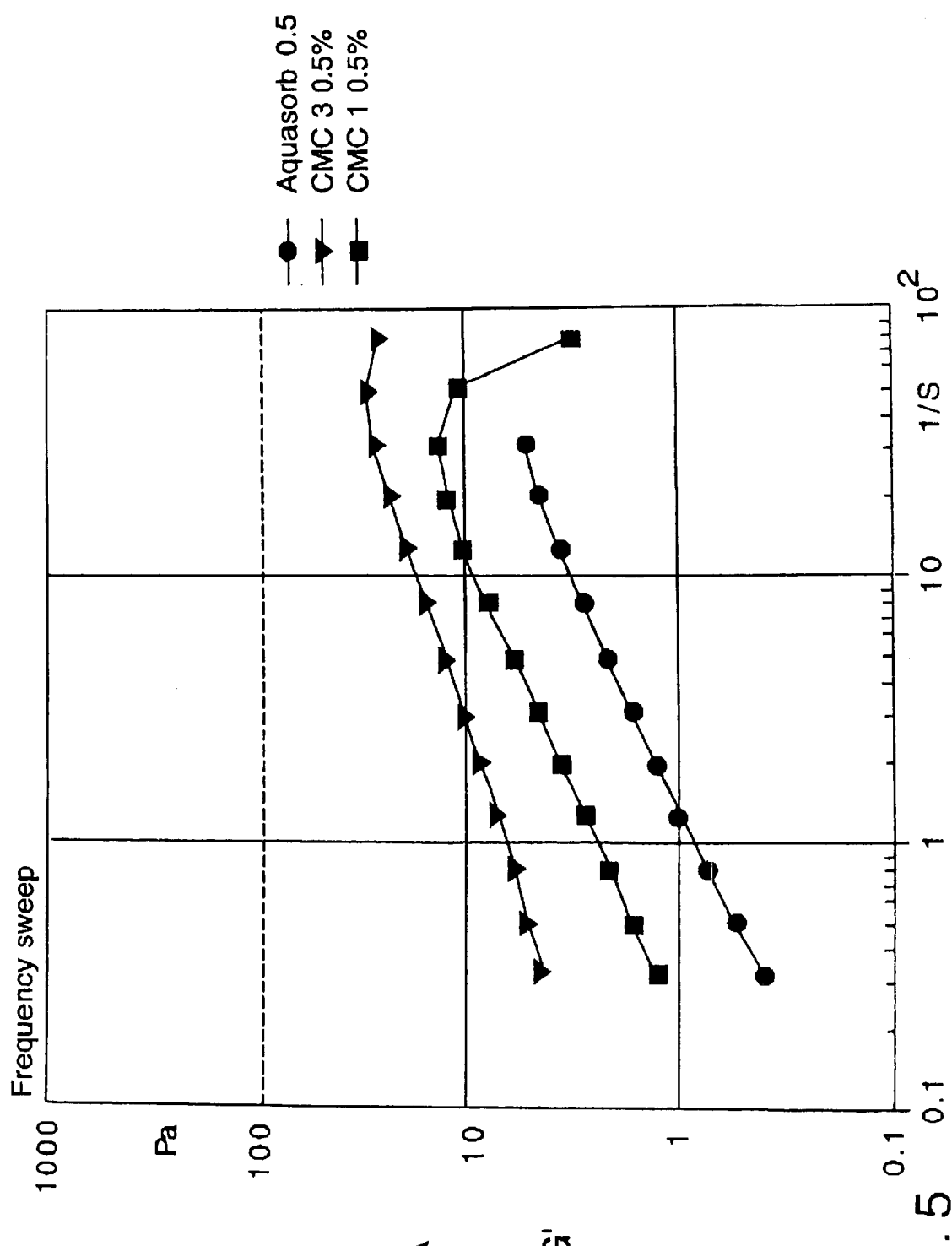
FIG. 5 shows product characterization by a very shallow increase in storage modulus and by its considerably higher storage modulus G".
Figure 6:
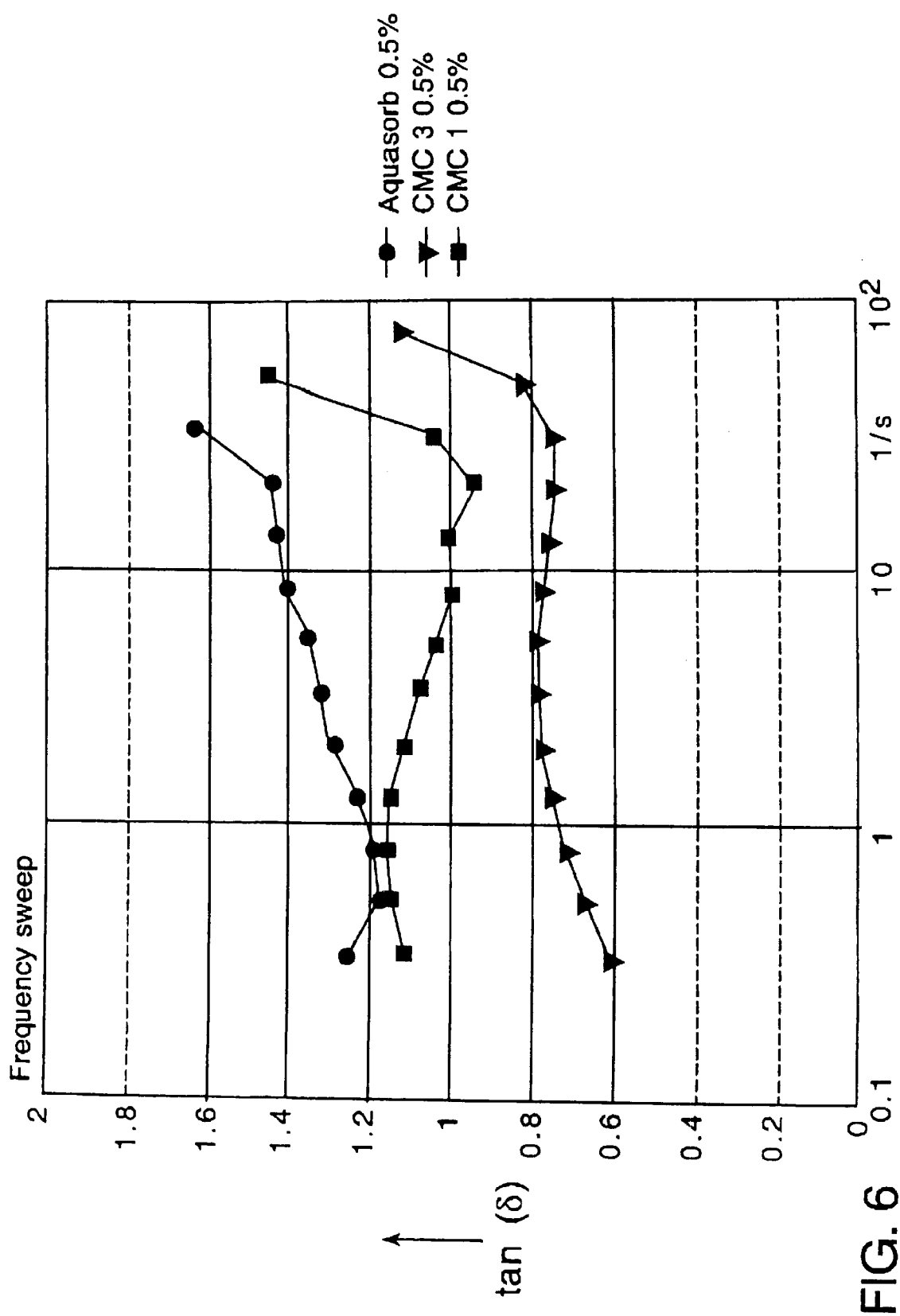
FIG. 6 shows the loss factor (tan δ) plotted against the angular frequency Ω.

The viscoelastic properties of the products were measured as a function of angular frequency Ω at a concentration of c=1% by weight and at a temperature of 25° C., using a viscometer controlled by shear stress (a CS 50 model manufactured by Bohlin, or a rotating viscometer manufactured by Physica, Stuttgart (Type UAS 200; FIGS. 5 and 6)). FIGS. 1–4 illustrate the storage modulus G', the loss modulus G", the complex viscosity η* and the phase angle δ as a function of angular frequency for the individual products.

The results which are presented in FIGS. 1–4 show that the products differ very considerably from each other as regards their viscoelastic properties. The flow behaviour of the Aquasorb sample at low frequencies is characterised by viscous flow (G">G'; the viscous component predominates over the elastic component). With increasing frequency, G' increases more sharply than G", so that the two curves intersect at a point. Above this point of intersection, the behaviour of the samples is determined by the elastic component. Samples CMC 1 and CMC 2 exhibit similar behaviour as regards their viscoelastic properties (modulus data, loss factor). The gel solidities of the solution structure or of the interlocking network are considerably less than that of the Aquasorb sample, however (G' values significantly less).

Rheologically, CMC No. 3 which is claimed according to the invention is completely different from the other samples. The elastic component G' is greater than the viscous component G" over almost the entire frequency range. This sample exhibits purely elastic behaviour. The product is characterised by a very shallow increase in storage modulus and by its considerably higher storage modulus G" over the entire frequency range (see FIG. 5 also).

FIG. 6 shows the loss factor (tan δ) plotted against the angular frequency Ω, which is denoted as the frequency sweep, for 0.5% by weight aqueous solutions of the CMC samples described in Table 1. Due to the high elastic component of the cellulose ethers which are claimed according to the invention, particularly CMC (see FIG. 6, CMC No. 3), the values of the loss factor are considerably less than those of the comparative samples, and this result is practically independent of angular frequency.

What is claimed is:

1. A substantially fibre-free cellulose ether wherein an aqueous solution of said cellulose ether having a maximum concentration of 0.5% by weight, exhibits a loss factor (tan δ) value of <1.0, at an angular frequency of 1 Hz.

2. The cellulose ether of claim 1 wherein said cellulose ether is selected from the group consisting of carboxymethyl cellulose ethers, sulphoethyl cellulose ethers, carboxymethylsulphoethyl cellulose ethers, methyl cellulose ethers, methylhydroxyethyl cellulose ethers, methylhydroxypropyl cellulose ethers, hydroxyethyl cellulose ethers and hydroxypropyl cellulose ethers.

3. The cellulose ether of claim 2 wherein said cellulose ether is selected from the group consisting of carboxymethyl cellulose ethers and sulphoethyl cellulose ethers.

4. The cellulose ether of claim 1 further wherein said cellulose ether has an absorbency of at least 30 g liquid/gram of cellulose ether; a particle size distribution, as adjusted by grinding and sieving, of 100%<2 mm, 100%<0.5 mm and at least 80%<0.075 mm; a viscosity of its 1% by weight water solution of at least 10,000 mPas as determined by a Brookfield, LVT, 30 rpm, spindle 4, at a temperature of 25° C., and water-soluble fraction of >99.0% (0.25% solution); a transmission of <99.9% as determined on a 0.5% by weight aqueous solution using a Hitachi spectrophotometer, optical path length d=10 mm, λ=550 nm.

5. The cellulose ether of claim 1 wherein said cellulose ether has a fibre content of less than 1%.

6. An article of manufacture comprising the cellulose ether of claim 1.

7. In the process for producing cellulose ether the improvement comprising using cellulose having an average degree of polymerization of at least 1000, an aqueous-organic suspension medium having a water content of 11 to 28 percent, an alkali present in an amount of 1.8 to 2.6 mole per mole of glucose, and an etherification agent present in an amount of 0.4 to 2.5 mole per mole of glucose, said percent being relative to the total volume of cellulose, suspension medium, alkali and etherification agent, wherein an aqueous solution of the cellulose ether produced by said process, having a maximum concentration of 0.5% by weight, exhibits a loss factor (tan δ) value of less than 1.0 at an angular frequency of 1 Hz.

8. The process of claim 7 wherein said aqueous organic suspension is at least one member selected from the group consisting of isopropanol-water, acetone-water, methanol-water, ethanol-water and tertiary-butanol-water.

9. The process of claim 7 wherein the water content is 12.5 to 25 percent.

10. The process of claim 7 wherein said alkali is sodium hydroxide.

11. The process of claim 7 wherein said etherification agent is monochloroacetic acid.

12. The process of claim 7 wherein the cellulose ether produced by said process is a carboxymethyl cellulose ether.

13. The process of claim 7 wherein the cellulose ether produced by said process has a fiber content of less than 1%.

* * * * *